(12) United States Patent
Wegdam et al.

(10) Patent No.: US 7,287,287 B2
(45) Date of Patent: Oct. 30, 2007

(54) SHOWER DEVICE WITH TANNING DEVICE AND METHOD FOR USE THEREOF

(75) Inventors: Pieter M Wegdam, HD Delft (NL); Oscar J Meijer, BD Delft (NL)

(73) Assignee: Sunshower B.V., Delft (NL)

( * ) Notice: Subject to any disclaimer, the term of this patent is extended or adjusted under 35 U.S.C. 154(b) by 292 days.

(21) Appl. No.: 10/505,695

(22) PCT Filed: Jul. 7, 2003

(86) PCT No.: PCT/NL03/00500

§ 371 (c)(1),
(2), (4) Date: Aug. 25, 2004

(87) PCT Pub. No.: WO2004/004830

PCT Pub. Date: Jan. 15, 2004

(65) Prior Publication Data

US 2005/0120474 A1   Jun. 9, 2005

(30) Foreign Application Priority Data

Jul. 5, 2002   (NL) ..................... 1021009

(51) Int. Cl.
*A47K 3/28* (2006.01)
(52) U.S. Cl. ................. 4/597; 4/614; 607/91
(58) Field of Classification Search ............... 4/597, 4/612, 614; 607/91; 250/504 R
See application file for complete search history.

(56) References Cited

U.S. PATENT DOCUMENTS

| 3,007,178 | A |  | 11/1961 | Altman et al. | 4/525 |
| 3,359,573 | A |  | 12/1967 | Casebolt | 4/607 |
| 4,095,113 | A |  | 6/1978 | Wolff | 250/494.1 |
| 4,130,120 | A |  | 12/1978 | Kohler, Jr. | 607/80 |
| 4,287,554 | A |  | 9/1981 | Wolff | 362/218 |
| 4,298,005 | A | * | 11/1981 | Mutzhas | 250/504 R X |
| 4,424,598 | A |  | 1/1984 | Cima | 4/524 |
| 4,623,796 | A |  | 11/1986 | Kratz | 250/504 R |
| 4,703,184 | A |  | 10/1987 | Wolff | 250/504 R X |
| 4,829,608 | A |  | 5/1989 | Stevens et al. | 4/597 |
| 4,835,749 | A | * | 5/1989 | Welton | 607/94 X |
| 6,139,568 | A |  | 10/2000 | Doty | 607/91 |
| 6,208,069 | B1 |  | 3/2001 | Jüstel et al. | 313/487 |
| 6,226,454 | B1 |  | 5/2001 | Couture | 392/419 |
| 6,265,835 | B1 |  | 7/2001 | Parra | 315/246 |
| 6,567,999 | B1 |  | 5/2003 | Thurner | 4/597 |
| 6,837,900 | B2 | * | 1/2005 | Ullrich et al. | 607/91 |

FOREIGN PATENT DOCUMENTS

| DE | 3025688 | 2/1982 |
| DE | 3500367 | 7/1986 |

(Continued)

*Primary Examiner*—Robert M. Fetsuga
(74) *Attorney, Agent, or Firm*—Van Dyke, Gardner, Linn & Burkhart, LLP

(57) ABSTRACT

The present invention relates to a shower device which is combined with a tanning device, comprising: one or more walls; water supply means which are arranged on one of the 5 walls; and a tanning device which is arranged in a wall and comprises at least one UV lamp, characterized in that the at least one UV lamp is a high-pressure UV lamp.

6 Claims, 4 Drawing Sheets

FOREIGN PATENT DOCUMENTS

| | | |
|---|---|---|
| EP | 0771543 | 5/1997 |
| GB | 2020970 | 11/1979 |
| GB | 2200549 | 8/1988 |
| WO | WO9217242 | 10/1992 |
| WO | WO0247526 | 6/2002 |

* cited by examiner

SHOWER DEVICE WITH TANNING DEVICE AND METHOD FOR USE THEREOF The present invention relates to a shower device comprising a tanning device with one or more UV lamps, a tanning device and a method for the use of such a shower device.

Known from WO 92/17242 are a method for tanning a person and a tanning device for this method. This is substantially a shower cubicle wherein fluorescent tubes for emitting UV light are arranged in the walls. A person can thus shower while the fluorescent tubes emit UV light, whereby this person simultaneously becomes browner. This known device has the drawback that the tanning distance is relatively low, and amounts to a maximum of 200 mm. A user will not become browner since during showering the distance from the lamps is always more than 200 mm. In addition, it is not possible to make the known device comply with the strict safety standards required in a wet environment such as a bathroom.

The present invention attempts to obviate the above stated drawbacks and has for its object to provide an improved shower device which is combined with a tanning device.

The present invention provides for this purpose a shower device, comprising:
one or more walls;
water supply means which are arranged on one of the walls; and
a tanning device which is arranged in a wall and comprises at least one UV lamp,
characterized in that
the at least one UV lamp is a high-pressure UV lamp.

Such a device offers all the advantages which are known according to the prior art, wherein the tanning distance is greater and can be large enough for use in a shower.

In a preferred embodiment the distance between the UV lamp and the wall in which it is arranged is greater than 40 mm, and preferably lies between 50 mm and 100 mm. Such a minimum distance increases safety, and has been found sufficiently safe for use in a wet environment such as a shower.

In a preferred embodiment the tanning device comprises reflector means which are arranged close to the one or more UV lamps, wherein the reflector means are arranged such that the tanning distance relative to the wall is between 150 mm and 650 mm, and is preferably in the order of 400 mm. Such a tanning distance has been found suitable for use in combination with a shower, so that a user can shower and tan simultaneously without having to stand uncomfortably close to the wall.

In a further preferred embodiment the tanning device comprises a plate closed watertight and at least partially UV permeable, which is arranged between the at least one UV lamp and the water supply means. The wall at the position of the tanning device is hereby erected from UV permeable material. Any wall which is seen as a (fixed) partition wall is suitable for placing therein of the tanning device.

The at least partly UV permeable plate further comprises a first filter plate. The use of the filter plate prevents the user being exposed to too much harmful radiation.

In a further preferred embodiment, the tanning device comprises air supply means and air discharge means, wherein during use of the UV lamps the supplied air is trained, for cooling thereof, at least partly along the filter plate and at least partly along the one or more UV lamps. The tanning device is safer through use of air cooling in the wall, as an adequate cooling is obtained so that the temperature of the filter plate is not allowed to be more than 40° C. higher than the ambient temperature.

In a further preferred embodiment, the tanning device comprises control means which comprise at least one clock and current interrupting means. The further advantage is hereby achieved that the time period of use is limited by the control means, thereby preventing the user from being exposed to too much harmful radiation.

In a further preferred embodiment the one or more high-pressure UV lamps are high-pressure gas discharge lamps.

According to a further aspect, the invention provides a tanning device for use in a shower device as described above.

According to yet another aspect, the invention provides a method for use of a shower device as described above.

Further advantages and features will be described with reference to the annexed drawings, in which.

Figure 4:
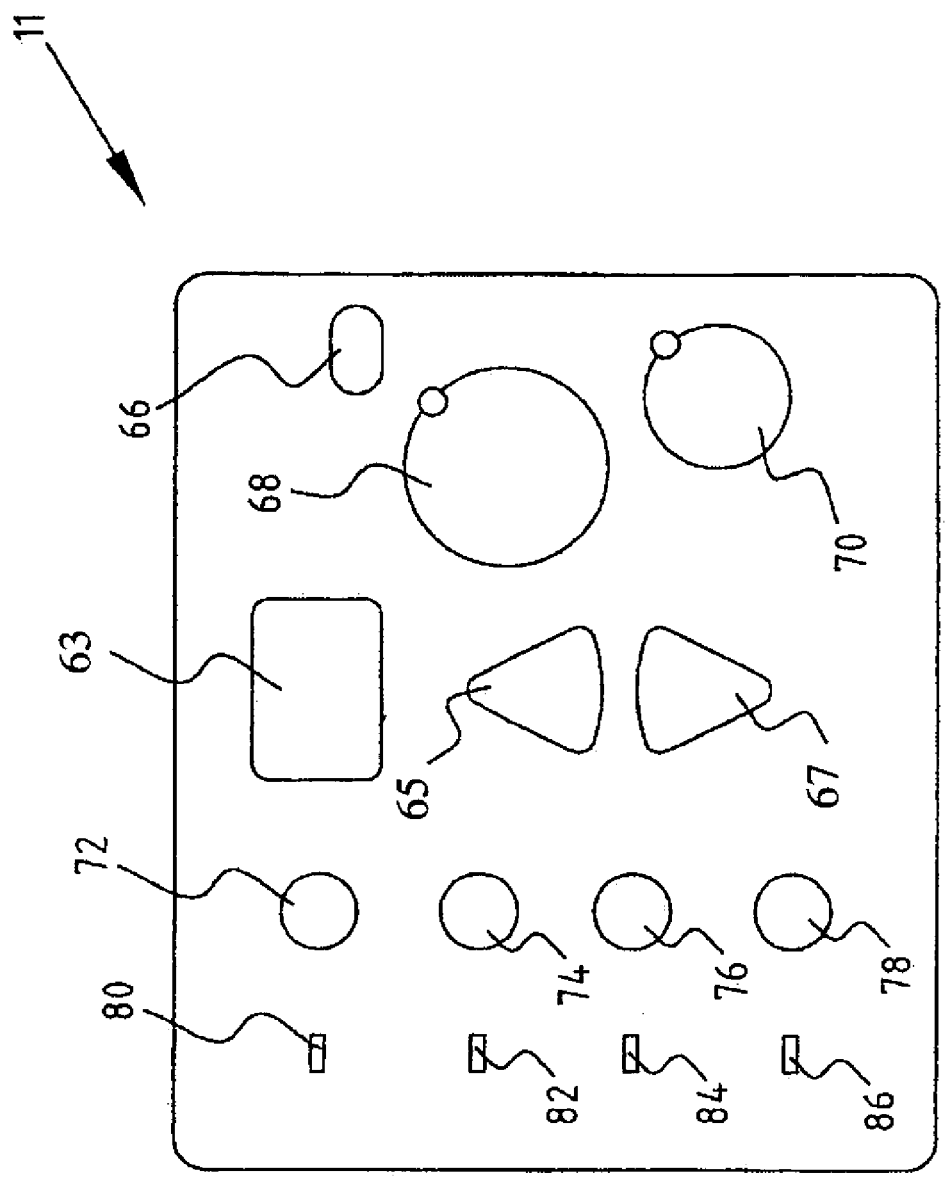
FIG. 4 shows a control panel of the tanning device in a preferred embodiment.

A shower device 1 in a preferred embodiment according to the invention comprises walls 2 and 3 which extend substantially vertically from a ground surface 4. A water supply means, here a shower head 5, is attached to wall 3. At some distance thereunder are arranged rotating taps 6 and 7 for regulating the flow rate and the temperature. Wall 2 is a pre-wall arranged in front of a house wall situated therebehind. In pre-wall 2 is arranged a tanning device 8, covered by a first filter plate 9 of hardened glass or of plastic. A frame 10 with watertight finish of plastic or metal provides the proper finish and appearance. Arranged inside the frame is a control panel 11 which is described with reference to FIG. 4. Control panel 11 is supported adjacent first filter plate 9.

Figure 1:
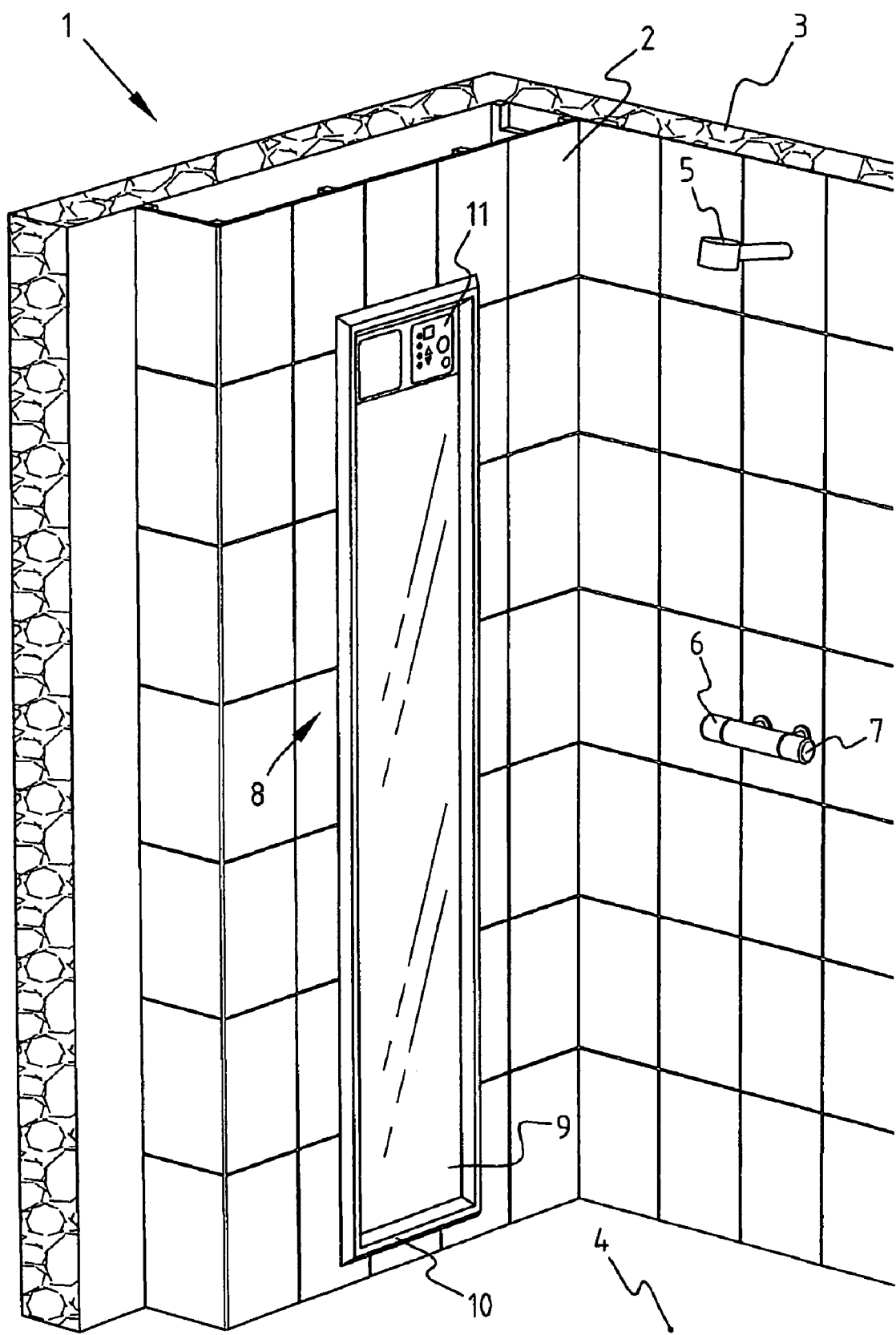
FIG. 1 shows a perspective view of a shower device according to the present invention in a preferred embodiment.
Figure 2:
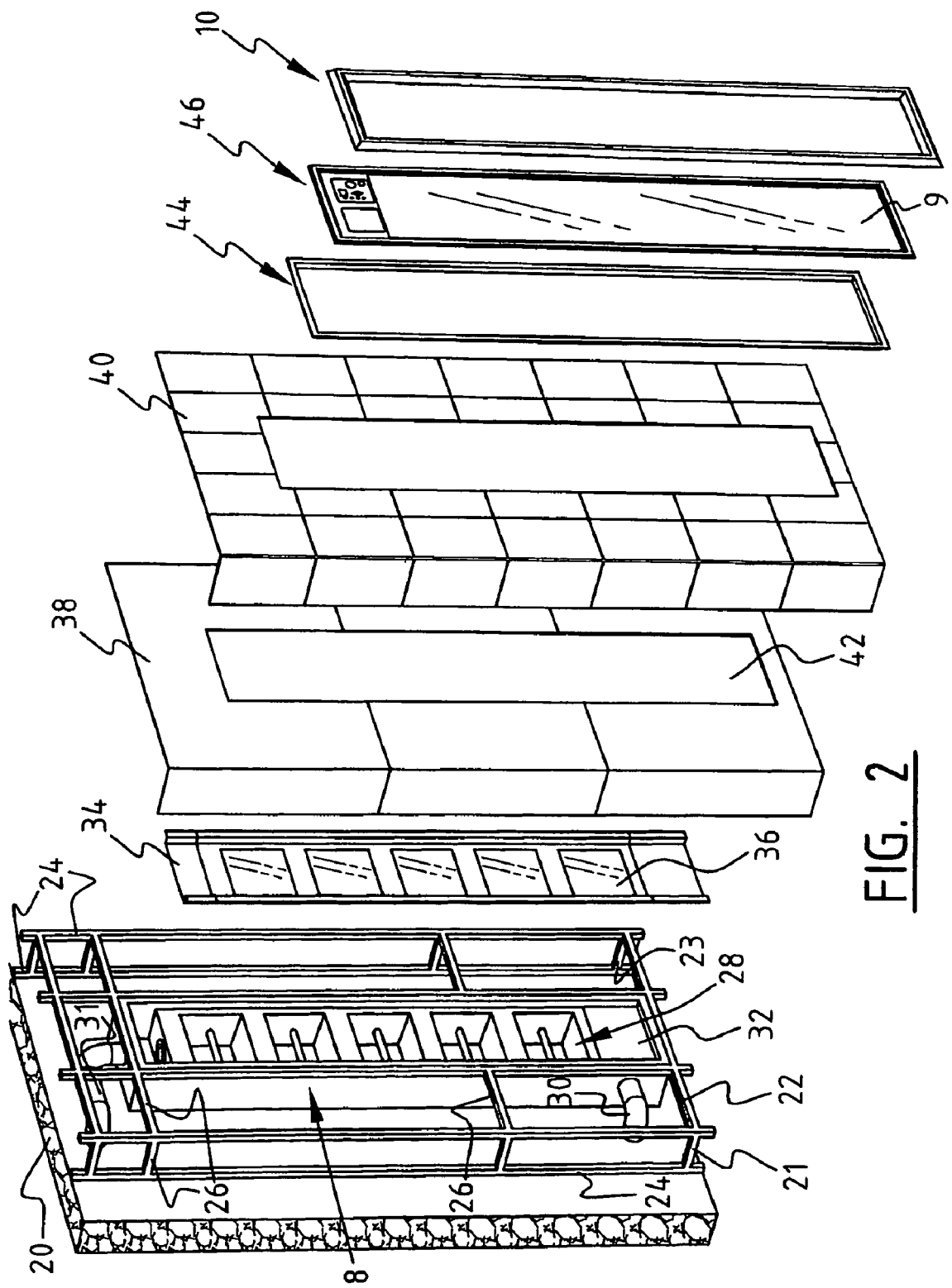
FIG. 2 shows a perspective exploded view of a wall with tanning device according to the present invention in a preferred embodiment.

The pre-wall (FIG. 2), a system which is supplied for different applications by for instance the company Geberit AG of Switzerland, is placed against a house wall 20 and comprises for instance three lower beams 21, 22, 23, wherein columns 24 are arranged vertically thereon in the shown embodiment. Horizontal beams 26 are arranged for strengthening purposes at the top and at suitable intermediate positions. Columns 24 and beams 22, 26 are mutually connected in a known manner which is further not shown. This construction extends as desired along the wall 20 in horizontal and/or vertical direction. Between the columns are arranged the tanning device 8 with UV lamps 28, for example high-pressure gas discharge lamps supplied by the Philips concern, Eindhoven (NL), under the name CLEO Swift HPA with a power of 250 to 500 W. Electric cables (not further shown) for supplying the lamps 28 with power are also accommodated in the pre-wall. As seen in FIG. 2, lamps 28 are arranged in a stacked vertical column.

Tubes 30, 31 are connected to fan 32 for feeding and discharging air to cool the UV lamps 28. The cooling of the filter plates is so effective that the temperature of the first filter plate 9 becomes less than 40° C. higher than the ambient temperature during use.

A frame 34 is arranged in front of reflectors 50. The filter plates 36 each screen one UV lamp in order to filter the radiation from the UV lamps. It is likewise possible that one larger filter plate screens all UV lamps simultaneously. Filter plate 9 likewise filters the radiation from the UV lamps and also serves for the watertight screening. At least one of the filter plates is preferably of coloured filter glass, so that the UV lamps are less bright, this being more pleasant during use. At least one of filter plates 9 and 36 also comprises a partly UV permeable hardened glass plate or a partly UV permeable plastic plate. There is a column of air between frame 34 and filter plate 9. Fan 32 ventilates this column, whereby the filter plates are cooled. The lamps and other components behind frame 34 are cooled by a separate fan (not shown).

Plaster panels 38 with tiles 40 thereon are arranged against the columns 24. In the plaster panels is arranged an elongate opening 42 for passage of light. In the opening 42 there is arranged a closing frame 44 on which is arranged a glass frame 46 having therein the first filter plate 9. Filter plate 9 lies in the same plane as the tiled wall or therebehind, wholly in accordance with the bathroom standards (Netherlands Standard NEN 1010). The unit is finished with the plastic or metal frame 10 (FIG. 2).

Figure 3:
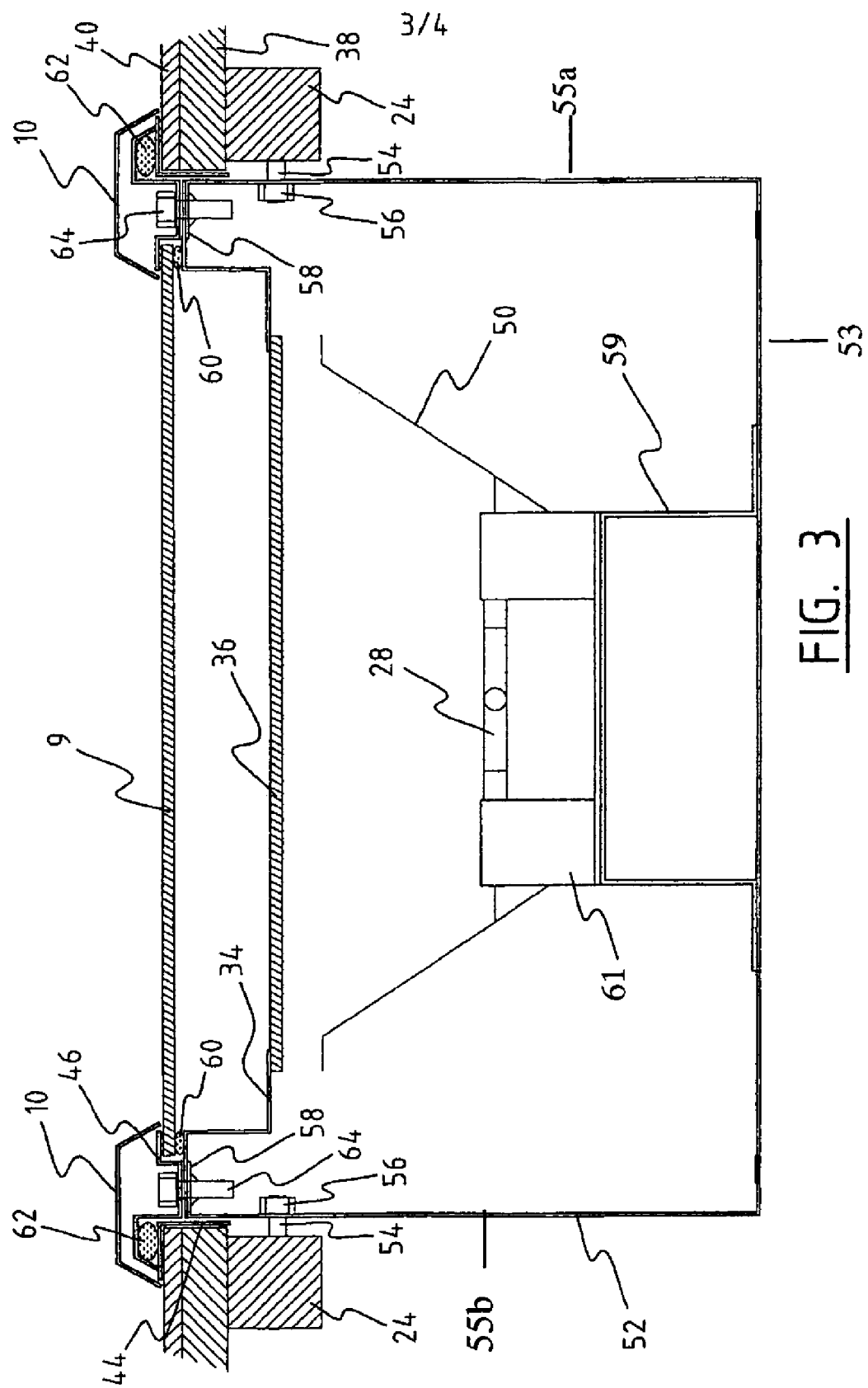
FIG. 3 is a schematic cross-section of the tanning device of FIG. 2.

Reflectors 50 of aluminum or stainless steel are arranged behind UV lamps 28 and supported adjacent associated tanning lamps 28 (FIG. 3). The reflectors are preferably of flat aluminum due to the better reflection. The ideal tanning distance from first filter plate 9 can be determined by varying the curvature of reflectors 50. The ideal tanning distance is between 150 mm and 650 mm, and is preferably in the order of 400 mm.

The installation process is as follows. The electricity and the ventilation ducts 30 and 31 are first constructed. Columns 24 and beams 22, 26 are then placed. Plaster panels 38 and tiles 40 are arranged against the columns and beams to form pre-wall 2, whereafter closing frame 44 is arranged along the edges of opening 42. Filter plate 36 is mounted to housing 52 wherein lamp 28, reflectors 50, housing 52 and plates 9 and 36 form an assembly to facilitate installation.

For a watertight assembly in the pre-wall, the tanning device comprises a housing 52 (FIG. 3) which is rectangular in top view and has an open front side. Housing 52 further includes a back wall 53 and a pair of opposing side walls 55a and b. Housing 52 is fastened to columns 24 with nuts 56. Against the rear side of the housing are arranged bent supports 59 on which lamp feet 61 are arranged, each with a UV lamp 28 and a reflector 50. Each lamp 28 has a longitudinal extent that extends between side walls 55a and b. Filter plates 36 are mounted to frame 34 and frame 34 is arranged against the bent edges 58 on the front of housing 52. The frame 46 with filter plate 9 therein is arranged against frame 34 and closing frame 44 in watertight manner using a suitable sealing agent 60, 62 such as cement, rubber or glue. Frames 34 and 46 are subsequently pressed more firmly against each other with bolts 64. The ornamental frame 10 is arranged for finishing purposes.

Owing to the above described watertight finishing, the tanning device can and may be connected to mains voltage. The minimum distance of preferably 4 cm, and more preferably 5 cm to 10 cm, between the wall or the filter plate 9 and the electrical provisions comprising the lamps and or the wiring thereof increases the safety.

The control panel 11 (FIG. 4) comprises a window 63 on which a period of time set using at least one button (or the middle buttons 65 and 67) can be read, after expiry of which the UV lamps are automatically switched off. Button 68 serves to switch on UV lamps 28. A stop button 70 is arranged with which the lamps can be switched off at a desired moment. Buttons 72, 74, 76 and 78 serve to switch on and off the five UV lamps arranged in this preferred embodiment, wherein light sources, such as LEDs 80, 82, 84 and 86, show respectively if the relevant UV lamp is switched on or off. Arranged behind window 66 is a LED which flashes when the lamps are cooling after use. Further built-in as a safety feature is that the current is interrupted after 30 minutes has passed.

The present invention is not limited to the above described preferred embodiment thereof; the rights sought are defined by the following claims, within the scope of which many modifications can be envisaged.

The invention claimed is:

1. A shower tanning device for use in a shower having a shower head, a floor and at least one fixed wall, said device comprising:
   a pre-wall adapted to be mounted inside the shower in front of a fixed wall in a position wherein the shower head is located outside of a first space defined between said fixed wall and said pre-wall when said pre-wall is mounted within said shower, said pre-wall including an opening having a periphery;
   a frame dimensioned to fit around the periphery of said opening;
   a housing positioned within said first space;
   a plurality of reflectors supported within said housing;
   at least one tanning lamp associated with and supported adjacent each of said reflectors, said reflectors positioned and arranged to direct light from said lamps through said opening;
   an inner filter positioned within said first space and associated with said lamps to filter some of the radiation being emitted by said lamps, said inner filter comprising a plurality of filter plates;
   an outer filter attached an outer filter frame and associated with said lamps to filter some of the radiation being emitted by said lamps, said outer filter mounted within said opening and spaced from said inner filter to thereby form a second space therebetween wherein said outer filter is cooler than said inner filter; and
   a watertight seal defined between said outer filter frame and said frame such that water from the shower head is prevented by said outer filter frame, said outer filter, and said watertight seal from entering into said first space and impinging said at least one tanning lamp and said reflectors.

2. The shower tanning device according to claim 1, wherein each of said filter plates is associated with at least one of said lamps.

3. A shower tanning device for use in a shower having a shower head, a floor and at least one fixed wall, said device comprising:
   a pre-wall adapted to be mounted inside the shower in front of a fixed wall in a position wherein the shower head is located outside of a first space defined between said fixed wall and said pre-wall when said pre-wall is mounted within said shower, said pre-wall including an opening having a periphery;
   a frame dimensioned to fit around the periphery of said opening;
   a housing positioned within said first space;
   a plurality of reflectors supported within said housing;
   at least one tanning lamp associated with and supported adjacent each of said reflectors, said reflectors positioned and arranged to direct light from said lamps through said opening, said lamps being arranged in a stacked vertical column;

an inner filter positioned within said first space and associated with said lamps to filter some of the radiation being emitted by said lamps an outer filter attached an outer filter frame and associated with said lamps to filter some of the radiation being emitted by said lamps, said outer filter mounted within said opening and spaced from said inner filter to thereby form a second space therebetween wherein said outer filter is cooler than said inner filter; and a watertight seal defined between said outer filter frame and said frame such that water from the shower head is prevented by said outer filter frame, said outer filter, and said watertight seal from entering into said first space and impinging said at least one tanning lamp and said reflectors.

4. A shower tanning device for use in a shower having a shower head, a floor and at least one fixed wall, said device comprising:

a pre-wall adapted to be mounted inside the shower in front of a fixed wall in a position wherein the shower head is located outside of a first space defined between said fixed wall and said pre-wall when said pre-wall is mounted within said shower, said pre-wall including an opening having a periphery;

a frame dimensioned to fit around the periphery of said opening;

a housing positioned within said first space;

a plurality of reflectors supported within said housing;

at least one tanning lamp associated with and supported adjacent each of said reflectors, said reflectors positioned and arranged to direct light from said lamps through said opening;

an inner filter positioned within said first space and associated with said lamps to filter some of the radiation being emitted by said lamps, said inner filter comprising a plurality of filter plates, each of said filter plates being mounted to said second frame;

an outer filter attached an outer filter frame and associated with said lamps to filter some of the radiation being emitted by said lamps, said outer filter mounted within said opening and spaced from said inner filter to thereby form a second space therebetween wherein said outer filter is cooler than said inner filter;

a watertight seal defined between said outer filter frame and said frame such that water from the shower head is prevented by said outer filter frame, said outer filter, and said watertight seal from entering into said first space and impinging said at least one tanning lamp and said reflectors; and a second frame surrounding said inner filter, said second frame arranged against said housing.

5. A shower tanning device for use in a shower having a shower head, a floor and at least one fixed wall, said device comprising:

a pre-wall comprising a plaster panel with tiles arranged thereon, said pre-wall adapted to be mounted inside the shower in front of a fixed wall in a position wherein the shower head is located outside of a first space defined between said fixed wall and said pre-wall when said pre-wall is mounted within said shower, said pre-wall including an opening having a periphery;

a frame dimensioned to fit around the periphery of said opening;

a housing positioned within said first space;

a plurality of reflectors supported within said housing;

at least one tanning lamp associated with and supported adjacent each of said reflectors, said reflectors positioned and arranged to direct light from said lamps through said opening;

an inner filter positioned within said first space and associated with said lamps to filter some of the radiation being emitted by said lamps an outer filter attached an outer filter frame and associated with said lamps to filter some of the radiation being emitted by said lamps, said outer filter mounted within said opening and spaced from said inner filter to thereby form a second space therebetween wherein said outer filter is cooler than said inner filter; and a watertight seal defined between said outer filter frame and said frame such that water from the shower head is prevented by said outer filter frame, said outer filter, and said watertight seal from entering into said first space and impinging said at least one tanning lamp and said reflectors.

6. A shower tanning device comprising:

a housing having a back wall, side walls extending from said back wall, and a front open side, and said housing being adapted for mounting in a shower;

a plurality of reflectors supported between said opposed side walls and mounted to said back wall;

at least one tanning lamp associated with and supported adjacent each of said reflectors, said reflectors being positioned and arranged to direct light from said lamps through said front open side of said housing, each of said tanning lamps having a longitudinal extent extending between said side walls of said housing;

a plurality of inner filter plates arranged against said housing, said inner filter plates associated with said lamps to filter some of the radiation being emitted by said lamps, said frame supporting said plurality of inner filter plates;

an outer filter plate arranged against said housing to filter some of the radiation being emitted by said lamps, said outer filter plate mounted over and spaced from said inner filter plate to thereby form a space therebetween wherein said outer filter plate is cooler than said inner filter plate.

* * * * *